(12) United States Patent
Edie

(10) Patent No.: US 8,083,800 B2
(45) Date of Patent: Dec. 27, 2011

(54) EXPANDABLE VERTEBRAL IMPLANT AND METHODS OF USE

(75) Inventor: Jason A. Edie, Salt Lake City, UT (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/687,674

(22) Filed: Jan. 14, 2010

(65) Prior Publication Data

US 2010/0114319 A1    May 6, 2010

Related U.S. Application Data

(62) Division of application No. 11/491,450, filed on Jul. 21, 2006, now abandoned.

(51) Int. Cl.
*A61F 2/44* (2006.01)

(52) U.S. Cl. .................... 623/17.16; 623/17.12

(58) Field of Classification Search .... 623/17.12–17.15, 623/17.11, 17.16; 606/246, 249, 247–248
See application file for complete search history.

(56) References Cited

U.S. PATENT DOCUMENTS

| | | | |
|---|---|---|---|
| 6,019,793 A * | 2/2000 | Perren et al. | 623/17.16 |
| 6,063,121 A * | 5/2000 | Xavier et al. | 623/17.15 |
| 6,447,543 B1 * | 9/2002 | Studer et al. | 623/17.11 |
| 7,156,848 B2 * | 1/2007 | Ferree | 606/261 |
| 7,320,708 B1 * | 1/2008 | Bernstein | 623/17.15 |
| 2003/0204271 A1 * | 10/2003 | Ferree | 623/61 |
| 2003/0220649 A1 * | 11/2003 | Bao et al. | 606/90 |
| 2004/0122517 A1 * | 6/2004 | Kuras | 623/17.11 |
| 2005/0027364 A1 * | 2/2005 | Kim et al. | 623/17.13 |
| 2005/0165486 A1 * | 7/2005 | Trieu | 623/17.13 |
| 2005/0197702 A1 * | 9/2005 | Coppes et al. | 623/17.12 |
| 2005/0228500 A1 * | 10/2005 | Kim et al. | 623/17.13 |
| 2008/0077244 A1 * | 3/2008 | Robinson | 623/17.16 |
| 2008/0147189 A1 | 6/2008 | Melkent | |
| 2008/0167726 A1 | 7/2008 | Melkent | |

* cited by examiner

*Primary Examiner* — Thomas C. Barrett
*Assistant Examiner* — Jan Christopher Merene

(57) ABSTRACT

An implant for insertion between vertebral members may include a first member with a first contact surface to contact the first vertebral member, and a second member with a second contact surface to contact the second vertebral member. A material may be secured to and extend between each of the first and second members. An interior space may be formed between the first and second members and the material. An inflatable member may be positioned within the interior space and may be inflatable upon the introduction of a substance into inflatable member. The inflatable member may be inflatable between a first size to space the first and second members a first distance apart and an enlarged second size to space the first and second members a second greater distance apart.

16 Claims, 7 Drawing Sheets

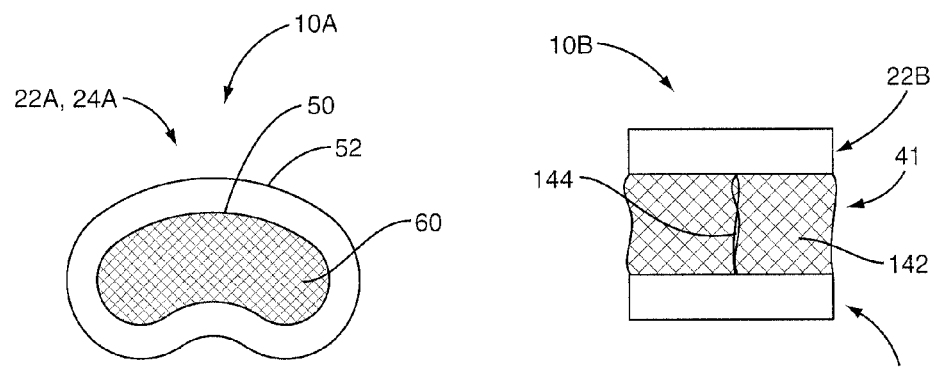
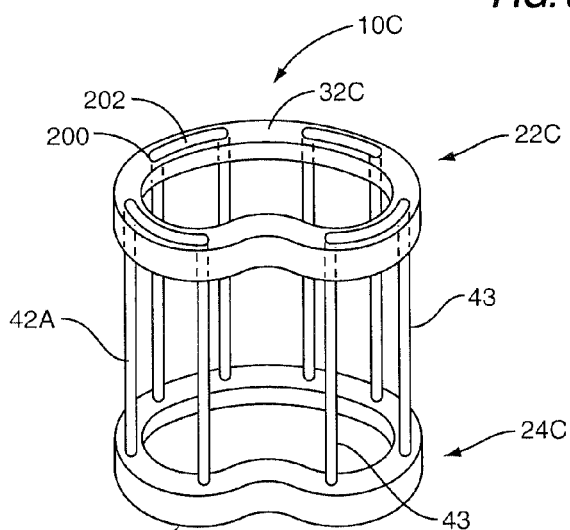
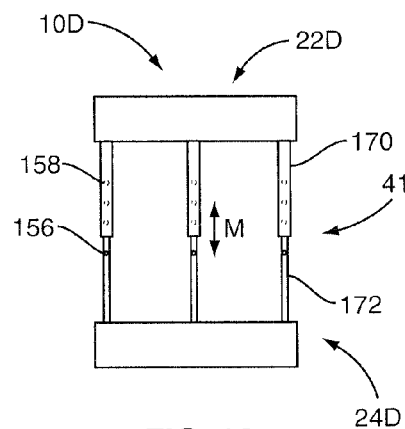

us 8,083,800 B2

EXPANDABLE VERTEBRAL IMPLANT AND METHODS OF USE

RELATED APPLICATIONS

The present application is a divisional application of U.S. patent application Ser. No. 11/491,450 filed on Jul. 21, 2006, herein incorporated by reference in its entirety.

BACKGROUND

Spinal implants are often used in the surgical treatment of spinal disorders such as degenerative disc disease, disc herniations, scoliosis or other curvature abnormalities, and fractures. Many different types of treatments are used, including the removal of one or more vertebral bodies and/or intervertebral disc tissue. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Regardless of the type of treatment and the type of implant used, surgical implantation tends to be a difficult for several reasons. For instance, access to the affected area may be limited by other anatomy. Further, a surgeon must be mindful of the spinal cord and neighboring nerve system. The size of the implant may present an additional obstacle. In some cases, a surgeon may discover that an implanted device has an inappropriate size for a particular application, which may require removal of the implant and insertion of a different implant. This trial and error approach may increase the opportunity for injury and is certainly time-consuming. Expandable implants are becoming more prevalent as a response to some of these concerns. However, the expansion mechanism in these devices tends to be complex and large. Consequently, existing devices do not appear to address each of these issues in a manner that improves the ease with which the device may be surgically implanted.

SUMMARY

Illustrative embodiments disclosed herein are directed to an implant for insertion between vertebral body endplates. The implant may include a first member with a first contact surface to contact the first vertebral member, and a second member with a second contact surface to contact the second vertebral member. A material may be secured to and extend between each of the first and second members. An interior space may be formed between the first and second members and the material. An inflatable member may be positioned within the interior space and may be inflatable upon the introduction of a substance into inflatable member. The inflatable member may be inflatable between a first size to space the first and second members a first distance apart and an enlarged second size to space the first and second members a second greater distance apart.

BRIEF DESCRIPTION OF THE DRAWINGS

FIG. 7 is a side view of a vertebral implant assembly according to one embodiment;

FIG. 8 is a top view of a vertebral implant assembly according to one embodiment;

FIG. 9 is a perspective view of one embodiment of a vertebral implant; and

FIG. 10 is a side view of a vertebral implant assembly according to one embodiment.

DETAILED DESCRIPTION

Figure 1:
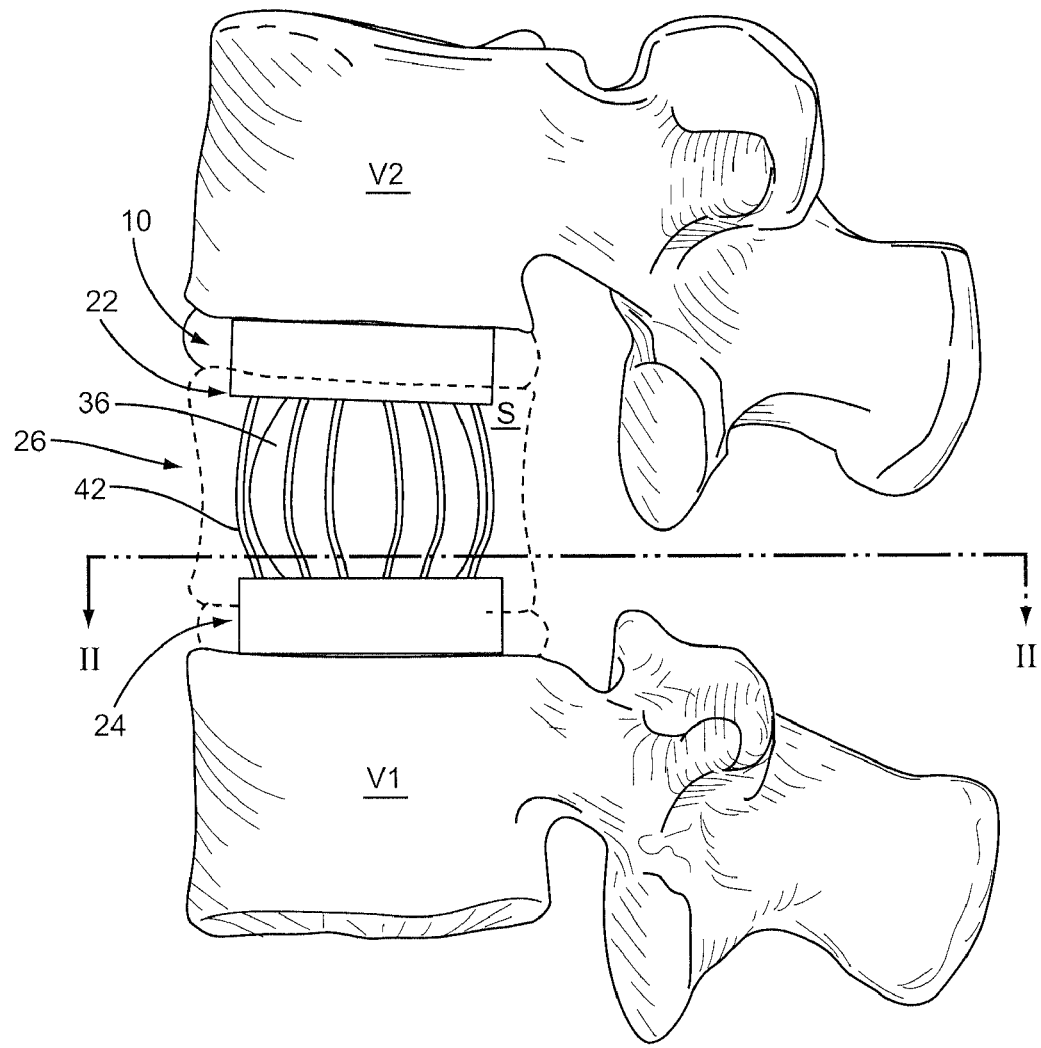
FIG. 1 is a side elevation view of a vertebral implant according to one embodiment positioned between vertebral bodies.

The various embodiments disclosed herein are directed to vertebral implants that are characterized by at least one expandable portion. The expandable portion may be assume a compressed first state during installation of the implant and may be expanded once the implant is positioned within the body. An exemplary implant 10 for supporting vertebral bodies is illustrated in FIG. 1. In one embodiment, the implant 10 is a vertebrectomy or corpectomy cage assembly positionable within an intervertebral space to span one or more vertebral levels along the longitudinal axis of the spinal column. Although the illustrated embodiment of the implant 10 spans one vertebral level, it should be understood that the implant 10 may be configured to span multiple vertebral levels.

Figure 2:
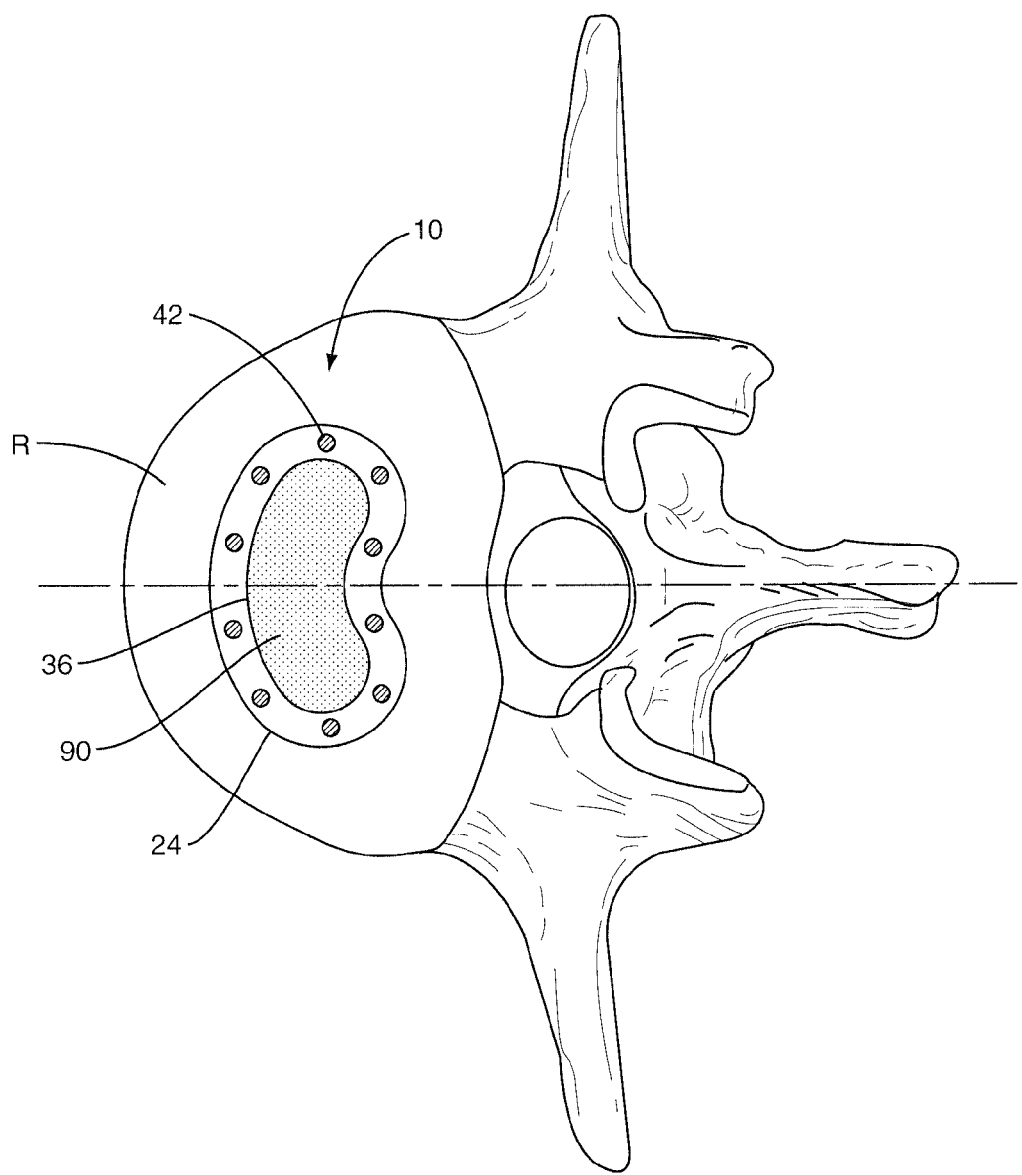
FIG. 2 is a section view of the vertebral implant according to the section lines in FIG. 1.
Figure 3:
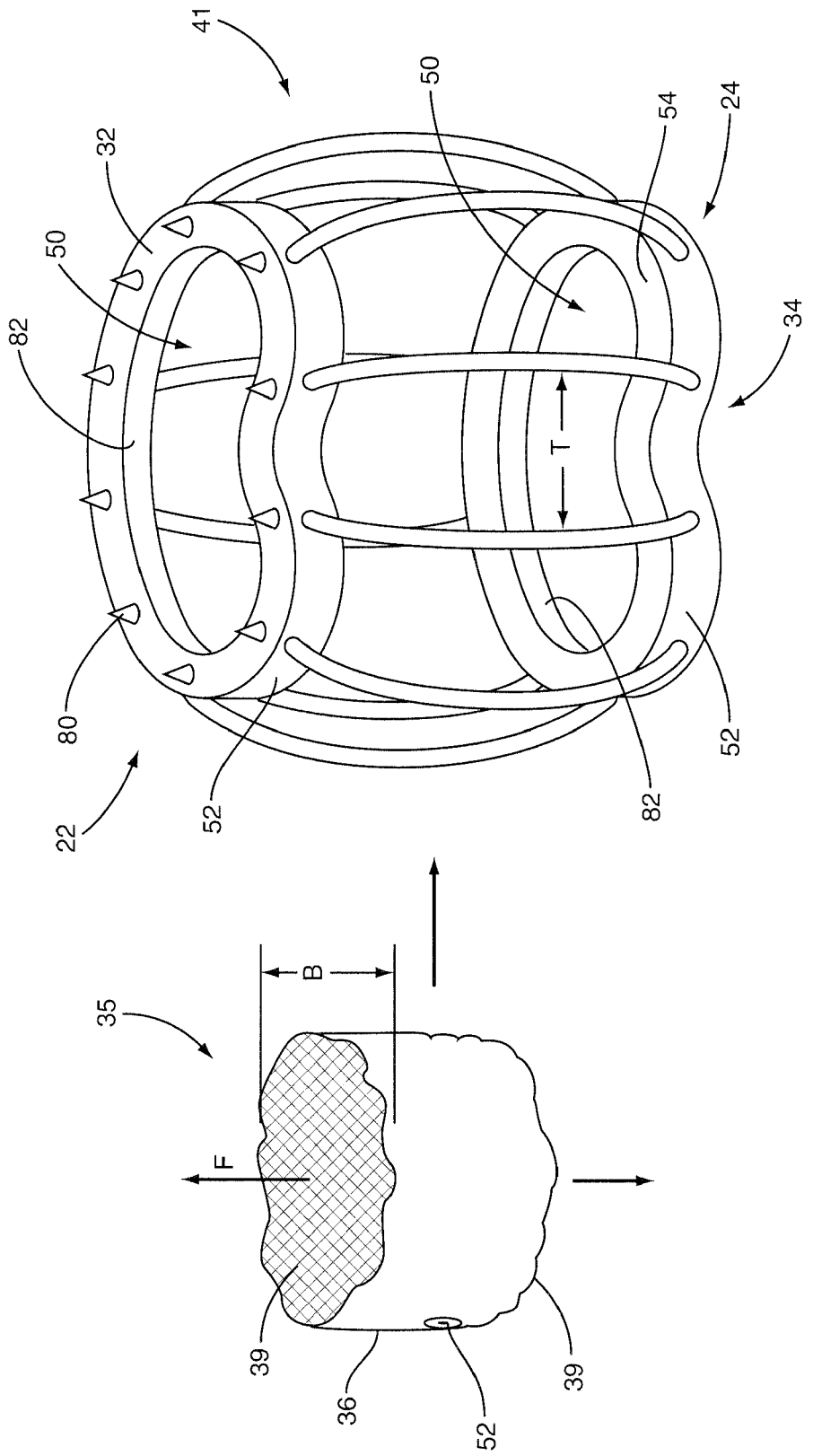
FIG. 3 is a perspective view of an exploded vertebral implant assembly according to one embodiment.

FIGS. 1-3 illustrate that the implant 10 generally includes a first end member 22, a second end member 24, and one or more expandable portions 26 between the first and second end members 22, 24. In one embodiment, the end members 22, 24 are formed of a biocompatible material, such as, for example, a carbon fiber material, or non-metallic substances, including polymers or copolymers made from materials such as PEEK and UHMWPE. In further embodiments, the end members 22, 24 may be formed of other suitable materials, such as, for example, stainless steel, titanium, cobalt-chrome, and shape memory alloys or other biocompatible metals.

The end members 22, 24 are adapted to engage the endplates of upper and lower vertebral bodies V1, V2. The expandable portion 26 is engaged between the end members 22, 24 to maintain an intervertebral axial space S between the upper and lower vertebral bodies V1, V2 following the removal of one or more vertebral levels (shown in phantom in FIG. 1). Generally, the expandable portion 26 includes a collapsible portion 41 and an inflatable portion 35. In the embodiment shown, the collapsible portion 41 includes a series of cords or tethers 42 and the inflatable portion 35 includes a balloon-like structure 36. A plurality of tethers 42 may extend around the perimeter 52 of the end members to form a cage. To facilitate insertion of the implant 10, the expandable portion 26 may be collapsed relative to the extended state shown in FIG. 1. Further details regarding process steps for insertion of the implant 10 are provided below.

The expandable portion 26 is expandable in a direction that is substantially transverse to the bone contact surfaces 32, 34 of the end members 22, 24. The bone contact surfaces 32, 34 of the end members 22, 24 may be planar or define surface features and/or a number of anchor elements 80 adapted for engagement with the vertebral endplates to inhibit movement of the end members 22, 24 relative to the vertebral bodies V1, V2. For example, in one embodiment, the bone contact surfaces 32, 34 may be roughened, such as, for example, by knurling and/or etching (e.g., photochemical etching). In other embodiments, various types of projections or protrusions may extend from the bone contact surfaces 32, 34, such as, for example, a number of spikes, ridges, teeth, axial grooves, checkerboard-type grooves, or any other type of anchoring element 80 that would occur to one of skill in the art. Although the bone contact surfaces 32, 34 of the end members 22, 24 are illustrated in FIGS. 1 and 3 as being arranged substantially planar, it should be understood that the bone contact surfaces 32, 34 may be tapered or curved to more closely conform with the anatomical curvature of the vertebral bodies V1, V2 at the surgical site.

In one or more embodiments, the implant 10 may be expanded through the introduction of an injectable substance that fills an inflatable balloon-like member 36, thereby causing the end members 22, 24 to move opposite one another. The number 90 in FIG. 2 identifies the injectable substance, which fills the balloon-like member 36. In the embodiment shown, the balloon-like member 36 includes a size and shape to fit within the end members 22, 24. Further, the balloon-like member 36 includes a compressed size (see dimension B) that is small enough to fit between adjacent tethers 42 (see dimension T) and an expanded size that is larger than the spacing between adjacent tethers 42. Accordingly, the expanded balloon-like member 36 is captively retained between the end members 22, 24 and inside the tethers 42.

The end members 22, 24 include similar shapes, which permits the end members 22, 24 to fit the vertebral bodies V1, V2 in a similar manner. The end members 22, 24 generally include respective bone contact surfaces 32, 34 and an opposing surface 54 facing opposite the bone-contact surfaces 32, 34, and a peripheral wall 52 extending therebetween. In the illustrated embodiment, the end members 22, 24 include a kidney shape, though other shapes may be used. In further embodiments, the end members 22, 24 may take on other types of configurations, such as, for example, a circular shape, semi-oval shape, bean-shape, D-shape, elliptical-shape, egg-shape, or any other shape that would occur to one of skill in the art. In other embodiments, the end members 22, 24 could also be described as being annular, U-shaped, C-shaped, V-shaped, horseshoe-shaped, semi-circular shaped, semi-oval shaped, or other similar terms defining an implant including at least a partially open or hollow construction. Thus, end members 22, 24 may be constructed for use in a variety of procedures, including but not limited to those requiring an anterior approach, a lateral approach, a posterior approach, or a trans-foraminal approach.

It should further be appreciated that the size and/or configuration of the end members 22, 24 may be specifically designed to accommodate any particular region of the spinal column and/or any particular vertebral level. For example, in embodiments associated with the upper thoracic or cervical region of the spine, the end members 22, 24 may be designed to have a D-shaped configuration, whereas embodiments associated with the lumbar region of the spine may be configured to have a horseshoe-shape, a U-shape, or other types of open-sided configurations.

In one embodiment, the end members 22, 24 have an outer profile that is substantially complementary to the size and shape of the peripheral portion or outlying region of the vertebral bodies V1, V2, such as the cortical rim or the apophyseal ring of the vertebral endplates. For example, as illustrated in FIG. 2, the outer perimeter of the end member 24 is preferably disposed generally above the inner edge of the cortical rim R of the vertebral body V1. In this manner, at least a portion of the end members 22, 24 is engaged against the cortical region of the vertebral endplates, thereby minimizing the likelihood of subsidence into the relatively softer cancellous region of the vertebral bodies V1, V2 following insertion of the implant 10 within the intervertebral space S.

Additionally, each of the bone contact surfaces 32, 34 may include one or more apertures or recesses 50 formed by an inner surface 82. The recess 50 is open at the bone contact surfaces 32, 34 and provided to enhance bony fusion between the end members 22, 24 and vertebral bodies V1, V2. The recesses 50 may be blind holes in that they do not extend through the end members 22, 24. The recesses 50 may be through-holes in that they do extend through the end members 22, 24. In one or more implementations, the implant 10 may be inserted in conjunction with bone growth materials that may include, for example, bone graft, bone morphogenetic protein (BMP), allograft, autograft, and various types of cement, growth factors and mineralization proteins. In a further embodiment, the bone growth promoting materials may be provided in a carrier (not shown), such as, for example, a sponge, a block, a cage, folded sheets, or paste. The bone growth materials may be loaded into the apertures 50 or generally applied to the bone-contact surfaces 32, 34.

The tethers 42 may be constructed of a complaint biocompatible material, such as a resin or polymer that may include materials such as nylon, polyethylene, polyurethane, silicone, polyethylene, polypropylene, polyimide, polyamide, and polyehteretherketone (PEEK). Further, the tethers 42 may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and Kevlar® may also be used. The tethers 42 may be cable-like, with a circular cross section or tape-like with a flattened cross section. Other cross sections may be possible or desirable, including for example, triangular, rectangular, polygonal, elliptical, or other cross sections. Furthermore, the tethers 42 may be secured to one or both of the end members 22, 24 using a variety of methods, including for example, tying, adhering, welding, or other methods that would occur to one skilled in the art.

The tethers 42 may be compliant in that they assume a shape that is determined by the spacing between the end members 22, 24. That is, the tethers 42 may be similar to a rope or thread and assume a random shape when the end members 22, 24 are brought in proximity to one another. In one embodiment, the tethers 42 are semi-rigid in that they assume a particular bent, curved, or splined shape to maintain a compressed height between the end members 22, 24. However, as the end members 22, 24 are pushed apart, such as by inflating the balloon-like structure 36, the tethers 42 will straighten to allow the end members 22, 24 to separate. Those skilled in the art will comprehend that a semi-rigid characteristic may be obtained through the use of flexible resin or composite materials or through the use of a thin metal filament, rod, or spring (not explicitly shown).

The balloon-like structure 36 may be constructed of a complaint biocompatible material, such as a resin or polymer that may include materials such as nylon, polyethylene, polyurethane, silicone, polyethylene, polypropylene, polyimide, polyamide, and polyehteretherketone (PEEK). The balloon-like structure 36 may be formed from materials that are used in other conventionally known biomedical applications, such as balloon angioplasty. Further, the balloon-like structure 36 may be reinforced with concentric layers of similar or dissimilar materials and/or fabrics (not specifically shown). For instance, a reinforcing structure may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and Kevlar® may also be used. Furthermore, the balloon-like structure 36 may be a separate member or may be secured to one or both of the end members 22, 24.

In one embodiment, the balloon-like structure 36 includes permeable end surfaces 39. That is, the end surfaces 39 include a perforated, grated, or mesh-like structure that allows the injectable substance 90 to pass from within the balloon-like structure 36 and through the apertures 50 to contact the corresponding vertebral bodies V1, V2 (see e.g., FIG. 1). In one embodiment, most or all of the balloon-like structure 36 is permeable in a similar manner. In one embodiment, no portion of the balloon-like structure is permeable (i.e., the injectable substance is substantially contained therein). The permeable nature of at least the end surfaces 39 makes it advantageous to include bone growth promoting materials within the injectable substance 90. Accordingly, as the injectable substance 90 is inserted into the balloon-like structure 36, the end members 22, 24 will expand under the influence of the expanding balloon-like structure 36. Additionally, some of the injectable substance 90 will exit the permeable end surfaced 39 and enter the apertures 50. Consequently, growth-promoting materials contained therein are positioned to enhance bone growth from adjacent vertebral bodies V1, V2 into the implant 10. In one embodiment, the permeable end surfaces 39 may be configured to contain the injectable substance 90 until a certain internal pressure is obtained. Beyond that pressure, obtained through introducing additional injectable substance 90, the injectable substance 90 will exit the end surfaces 39 and enter the apertures 50.

Various techniques may be used to introduce an injectable substance 90 into the balloon-like structure 36. In the embodiment shown, a fill port 52 is provided on the balloon-like structure 36. Notably, while only one fill port 52 is depicted, additional ports 52 may be used. Further, the port 52 may be located in different locations depending on a particular implementation and angle of approach. The fill port 52 may be attached to a syringe or other pumping mechanism (see FIGS. 4-6) to fill the balloon-like structure 36. An injectable substance may flow through the fill port 52 into the interior volume of the balloon-like structure 36. As the injectable substance fills the balloon-like structure 36, the ends 39 of the balloon-like structure 36 extend to contact the end members 22, 24 and may expand to fill the recesses 50 formed within the end members 22, 24. As the ends 39 of the balloon-like structure 36 expand, they exert a displacement force F that causes the end members 22, 24 to separate from one another. Furthermore, fill port 52 may include a self-sealing valve (not specifically shown) that prevents the injectable substance from flowing in one direction or another once the balloon-like structure 36 is filled.

A variety of injectable substances may be inserted into the balloon-like structure 36 to cause the end members 22, 24 to separate. In one embodiment, the injectable substance is a fluid, such as a gas or a liquid. In one embodiment, the injectable substance is a solid, such as a powder. In one embodiment, the injectable substance is a curable liquid that solidifies after a predetermined amount of time or under the influence of an external catalyst. For instance, an injectable liquid may cure under the influence of heat or light, including ultraviolet light. Some examples of in situ curable liquids include epoxy, PMMA, polyurethane, and silicone. A curable substance may cure to a substantially rigid state or to a flexible, but relatively incompressible state.

Figure 4:
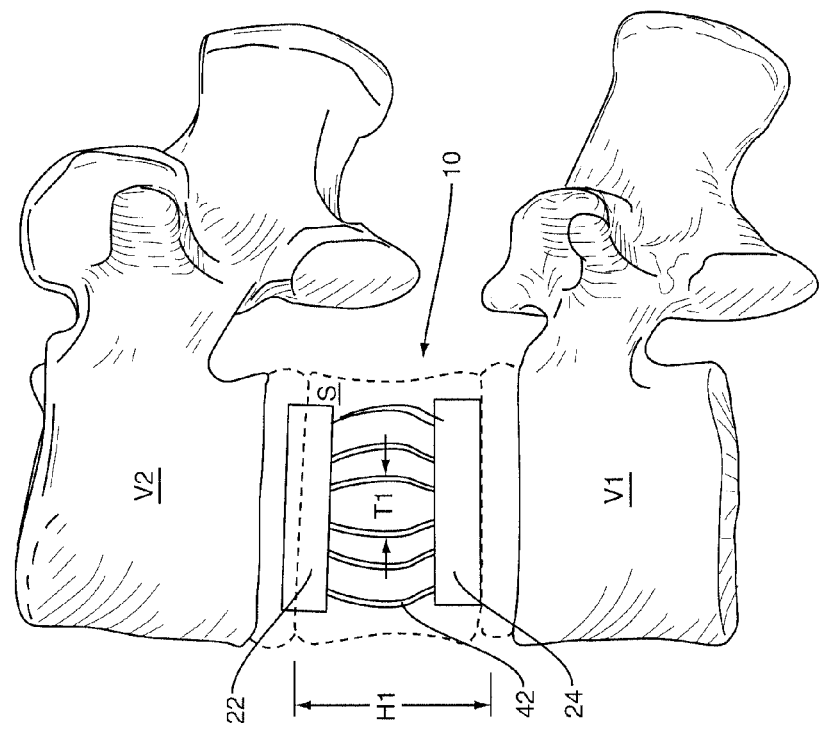
FIGS. 4-6 illustrate a sequence of implantation steps to obtain a desired vertebral body spacing, each Figure depicting a lateral view of a vertebral implant according to one or more embodiments shown relative to vertebral bodies.
Figure 4:
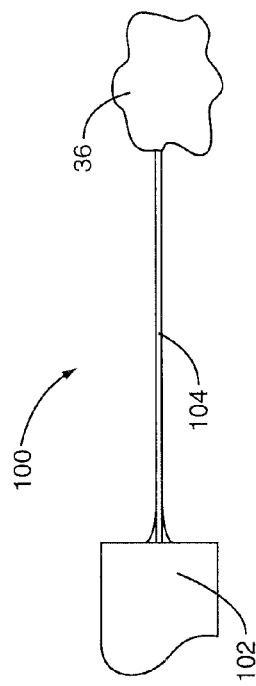
Figure 5:
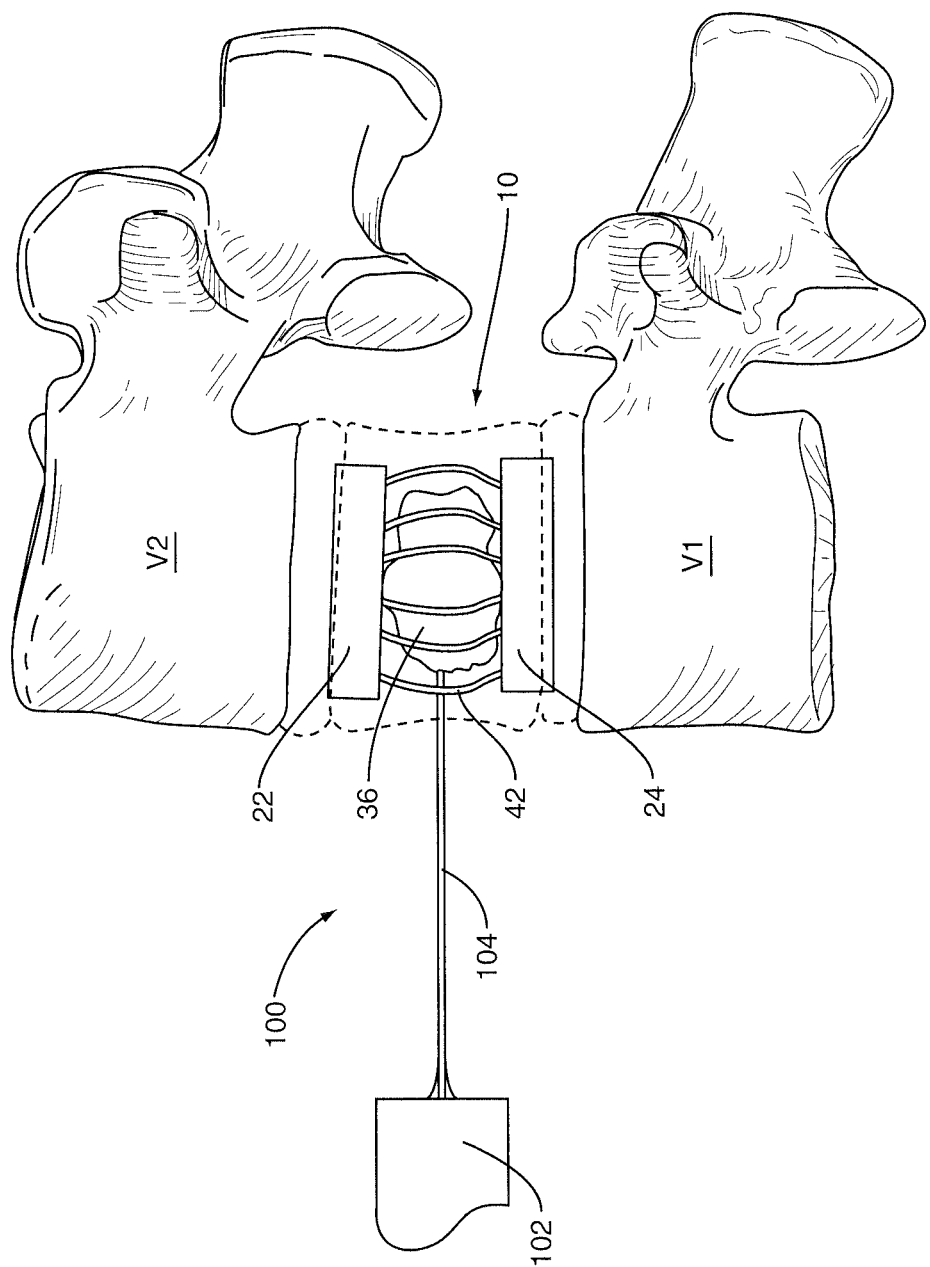
Figure 6:
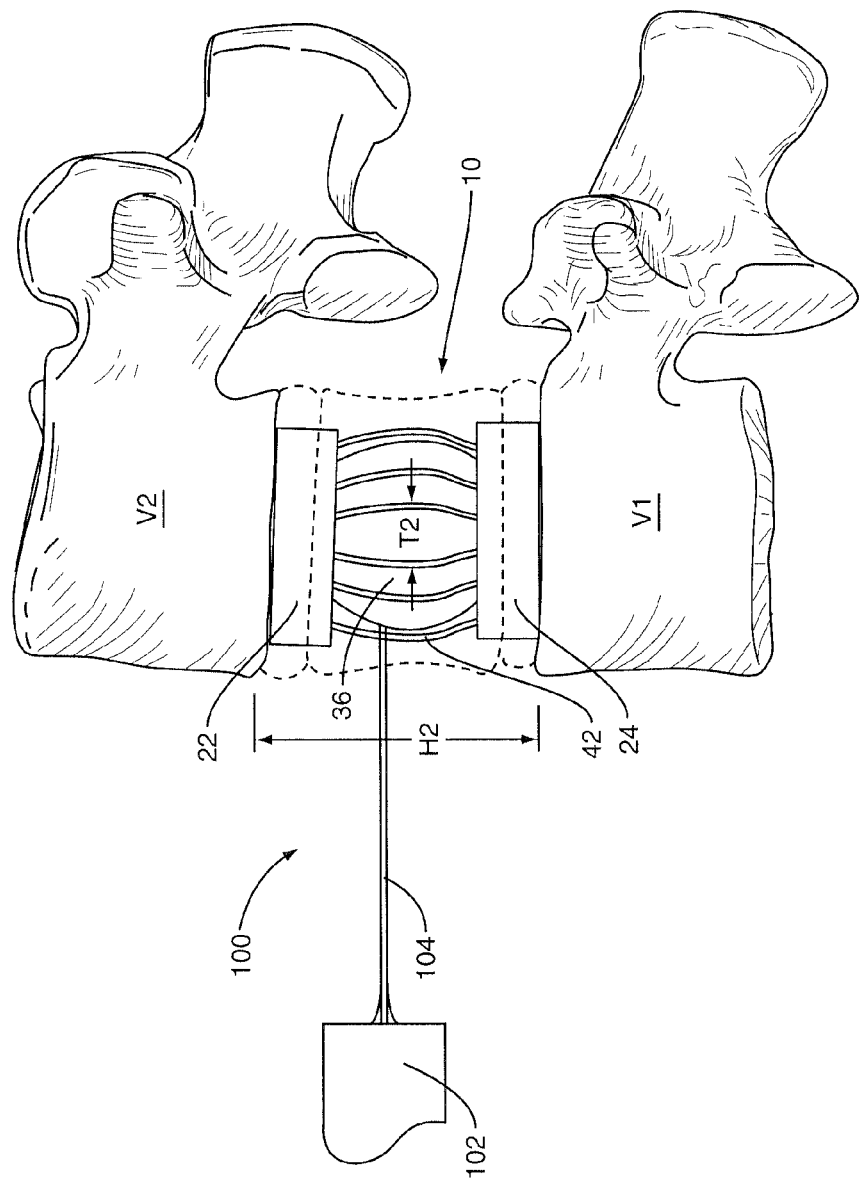

The implant 10 may be inserted into a patient according to the process steps illustrated in FIGS. 4-6. In FIG. 4, the implant 10 is inserted in a compressed first state including a first height H1 and positioned within an intervertebral space formed after the removal of one or more vertebrae or discs. Once the implant 10 is positioned as shown in FIG. 4, the inflation tool 100 or other injection instrument is used to position the balloon-like structure 36 and inject the injectable substance into the fill port 52 on the balloon-like structure 36. As suggested above, the balloon-like structure 36 is collapsed and is able to fit between end members 22, 24 through the spacing T1 between tethers 42. Note that in the collapsed first state with a height H1, the tethers 42 may be compliant and may be separated to insert the balloon-like member 36.

In one embodiment, a single tool 100 is used to position and fill the balloon-like structure. In one embodiment, the balloon-like structure is positioned between the end members 22, 24 using a different tool (not shown) than the inflation tool 100. In one embodiment, the balloon-like member 36 is pre-positioned between the end members 22, 24 and inserted into the intervertebral space along with the end members 22, 24.

The inflation tool 100 may be implemented as a syringe-like structure including a reservoir portion 102 and a delivery portion 104. The delivery portion 104 is configured to engage the fill port 52 to transfer the injectable substance from the reservoir portion 102 into the balloon-like structure 36. Other delivery mechanisms are certainly appropriate. For instance, pneumatic or hydraulic fittings may be appropriate. The delivery portion 104 may be implemented as a needle, as tubing, or other cannulated devices. In any event, as the injectable substance is introduced into the implant 10, the end members 22, 24 are forced apart due to the expansion of the contained balloon-like structure 36. Ultimately, the implant 10 is expanded to an expanded second state including a second height H2 as shown in FIG. 6. In the expanded second state with a height H2, the tethers 42 may pulled somewhat taught and the spacing T2 between adjacent tethers is sufficiently maintained to captively retain the balloon-like member 36.

FIG. 7 depicts a top (or bottom) view of an exemplary end member 22A or 24A for use in the vertebral implant 10. In previous embodiments, the end members 22, 24 included an open recess 50. In the embodiment illustrated in FIG. 7, the recess 50 is covered by a permeable member 60 that provides a physical barrier to expansion by the balloon-like structure but that permits fluid flow and bony ingrowth. The permeable member 60 may be constructed of a braided or mesh-like biocompatible material, such as a resin or polymer that may include materials such as nylon, polyethylene, polyurethane, silicone, polyethylene, polypropylene, polyimide, polyamide, and polyehteretherketone (PEEK). Further, the permable member 60 may be reinforced with layers of similar or dissimilar materials and/or fabrics (not specifically shown). For instance, a reinforcing structure may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and Kevlar® may also be used.

In embodiments described above, the expandable portion 26 included a collapsible portion 41 comprised of a series of cords or tethers 42. In the embodiment shown in FIG. 8, the collapsible portion 41 includes a mesh-like member 142 that is secured to end members 22B, 24B. The mesh-like member 142 is generally compliant and may be collapsed and extended to permit the overall implant 10B to assume compressed and extended heights H1, H2 as shown in FIGS. 4 and 6. The mesh-like member 142 may be constructed from materials disclosed herein or using a variety of other biocompatible materials known to those skilled in the art. The mesh-like member 142 is provided with an opening 144 through which the balloon-like member 36 may be inserted. As with the previously-described tethers 42, the opening 144 is advantageously sized to permit a collapsed balloon-like member 36 to pass, but small enough to prevent an inflated balloon-like member 36 from escaping.

FIG. 9 depicts an embodiment of an implant 10C similar to the embodiments depicted in FIGS. 1-3. However, in the present embodiment, the tether 42A is provided as a continuous member that is threaded through and between the illustrated end members 22C, 24C. Note that the single tether 42A is threaded through the end members 22C, 24C with individual runs 43 of the tether 42A functioning as the separate tethers 42 in above-described embodiments. The illustrated tether 42A may be implemented as a continuous member, passing through tether holes 200 and at least partially passing through tether channels 202 in the end members 22C, 24C. Notably, the channels 202 may be recessed below the bone-contact surfaces 32C, 34C to allow the bone-contact surfaces 32C, 34C to directly contact the corresponding endplates on the vertebral bodies. The ends of the tether 142 may be secured to each other using a variety of methods, including for example, tying, adhering, crimping, soldering, welding, or other methods that would occur to one skilled in the art.

FIG. 10 depicts an embodiment of an implant 10D in which the collapsible portion 41 includes sliding and telescoping attachment members 170, 172, respectively. In one embodiment, the attachment members 170, 172 are rigid and capable of axially sliding relative to one another according to the arrows labeled M. Further, because the attachment members 170, 172 are rigid, the end members 22D, 24D are maintained in a predetermined alignment relative to each other. In one embodiment, attachment members 170, 172 are flexible members that are capable of axially sliding relative to one another as well as lateral bending. Consequently, the end members 22D, 24D remain coupled, but are movable relative to each other in multiple directions.

In certain implementations, where the injectable substance remains fluid or takes an extended period of time to cure, the end members 22D, 24D are provided with position locks 156, 158. In one embodiment, attachment member 172 includes protruding features 156 and attachment member 170 includes recessed features 158 disposed at various heights about the interior thereof. Thus, when the attachment members 170, 172 are joined to one another, the protruding features 156 engage the recessed features 158 to provide a locked height that prevents compression of the implant 10D. That is, as the balloon-like structure 36 is filled with an injectable substance, the end members 22D, 24D will separate and expand to a position where a protrusion 156 engages a recess 158. At this point, introducing additional injectable substance will force the protrusion 156 to disengage from the recess 158 and ultimately engage a next higher recess 158. The protrusions 156 and/or the recesses 158 may be angled, tapered, or oriented to permit expansion of the implant 10D but not compression in the reverse direction. Those skilled in the art will comprehend a variety of ways to implement this type of unidirectional locking. The protruding features 156 may be implemented using a variety of features, including but not limited to ball plungers, expanding pegs, protruding stops, and shape-memory alloys. In the latter case, the protruding features 156 may be positioned in a first retracted position and then, upon the application of elevated temperatures (which may be provided by body temperatures), the protruding feature 156 will expand to engage a recess 158 corresponding to a desired implant height.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the embodiments disclosed herein have contemplated a single implant positioned between vertebral bodies V1, V2. In other embodiments, two or more smaller implants may be inserted between the vertebral bodies V1, V2. The present embodiments are, therefore, to be considered in all respects as illustrative and not restrictive, and all changes coming within the meaning and equivalency range of the appended claims are intended to be embraced therein.

What is claimed is:

1. An implant for insertion between first and second vertebral members comprising:
   a first end member with a first contact surface to contact the first vertebral member;
   a second end member with a second contact surface to contact the second vertebral member, the second end member being spaced away from the first end member;
   a compliant mesh material secured to and extending between each of the first and second end members;
   an interior space formed between the first and second end members and the mesh material;
   the mesh material having a uniform construction around central regions of the end members that is interrupted by not more than one opening that extends into the interior space;
   an inflatable member positioned within the interior space and being inflatable upon the introduction of a substance into the inflatable member, the inflatable member being inflatable between a first size to space the first and second end members a first distance apart and an enlarged second size to space the first and second end members a second greater distance apart;
   the inflatable member being separate from the mesh material;
   the opening being larger than the first size of the inflatable member and smaller than the second size of the inflatable member.

2. The implant of claim 1, wherein the mesh material includes a smaller collapsed height when the inflatable member is in the first size, and a larger extended height when the inflatable member is in the second size.

3. The implant of claim 1, wherein each of the first and second end members includes a continuous perimeter that extends around and encloses a recess that is in communication with the interior space.

4. The implant of claim 3, wherein the inflatable member includes permeable end surfaces that align with the recesses in the first and second end members and are exposed to the vertebral members when the inflatable member is in the second size.

5. The implant of claim 1, wherein the mesh material is secured about a perimeter of the first and second end members.

6. The implant of claim 1, wherein the mesh material is in the form of a sheet with a first edge positioned at the first end member and an opposing second edge positioned at the second end member.

7. An implant for insertion between first and second vertebral members comprising:
   a first end member with a first contact surface to contact the first vertebral member;
   a second end member with a second contact surface to contact the second vertebral member;
   an interior space formed between the first and second end members;
   a material secured to and extending between each of the first and second end members, the material enclosing sides of the interior space between the first and second end members and being spaced away from central regions of the end members;
   the material having a uniform construction around central regions of the end members that is interrupted by not more than one opening that extends into the interior space;
   an expandable member positioned within the interior space and being adjustable between an expanded size and an unexpanded size;
   the material being reconfigurable upon expansion of the expandable member from a first size that spaces the first and second end members a first distance apart and an enlarged second size that spaces the first and second end members a second greater distance apart;
   wherein the opening is sized to allow the expandable member to pass therethrough when the first size but block the expandable member from passing therethrough when the second size;
   wherein all portions of the first end member are farther from all portions of the second end member when the first and second end members are at the second distance apart than when the first and second end members are at the first distance apart.

8. The implant of claim 7, wherein the material extends around lateral sides of the interior space and forms a perimeter of the interior space.

9. The implant of claim 7, wherein each of the first and second end members includes an annular shape with a recess that is in communication with the interior space.

10. The implant of claim 7, wherein the material is secured about a perimeter of the first and second end members.

11. The implant of claim 7, wherein the material is tighter when the expandable member is in the second size than in the first size.

12. The implant of claim 7, wherein the material is a compliant mesh.

13. An implant for insertion between first and second vertebral members comprising:
   a first end member with a first contact surface to contact the first vertebral member;
   a second end member with a second contact surface to contact the second vertebral member;
   an intermediate space formed between the first and second end members;
   a material secured to and extending between each of the first and second end members, the material forming lateral sides of the intermediate space between the first and second end members;
   an expandable member positionable within the intermediate space and being movable from an unexpanded size to an enlarged expanded size to spread apart the first and second end members;
   not more than one opening in the material; wherein the opening is sized to allow the expandable member to pass therethrough when in the unexpanded size but block the expandable member from passing therethrough when in the expanded size;
   the material being secured to the end members prior to insertion of the expandable member through the opening and into the interior space;
   the material having a uniform construction that is interrupted by the opening.

14. The implant of claim 13, wherein each of the first and second end members includes an annular shape with a recess that is in communication with the intermediate space.

15. The implant of claim 14, wherein the expandable member includes permeable end surfaces that align with the recesses in the first and second end members and are exposed to the vertebral members when the expandable member is in the second size.

16. The implant of claim 14, wherein the material is a sheet that is secured about a perimeter of the first and second end members.

* * * * *